(12) United States Patent
Bao et al.

(10) Patent No.: US 7,874,213 B2
(45) Date of Patent: Jan. 25, 2011

(54) ULTRASONIC TEST APPARATUS

(75) Inventors: Shan-Qin Bao, Shenzhen (CN); Wei Chen, Shenzhen (CN)

(73) Assignees: Hong Fu Jin Precision Industry (ShenZhen) Co., Ltd., Shenzhen, Guangdong Province (CN); Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 372 days.

(21) Appl. No.: 12/168,899

(22) Filed: Jul. 8, 2008

(65) Prior Publication Data

US 2009/0114023 A1    May 7, 2009

(30) Foreign Application Priority Data

Nov. 6, 2007    (CN) .................. 2007 1 0202407

(51) Int. Cl.
*G01N 29/04*    (2006.01)
(52) U.S. Cl. .............. 73/627; 73/600; 73/606; 73/620
(58) Field of Classification Search .......... 73/627, 73/606, 618, 620, 629, 599, 600, 602
See application file for complete search history.

(56) References Cited

U.S. PATENT DOCUMENTS

| | | | | |
|---|---|---|---|---|
| 3,291,271 A | * | 12/1966 | Trimmer .................. 192/58.2 |
| 4,821,753 A | * | 4/1989 | Nakamura et al. ............ 134/59 |
| 5,302,856 A | * | 4/1994 | Narita et al. ................. 257/788 |
| 5,359,895 A | * | 11/1994 | Isenberg et al. ............... 73/582 |
| 5,372,042 A | * | 12/1994 | Jarman et al. ................. 73/588 |
| 5,600,068 A | * | 2/1997 | Kessler et al. ................. 73/620 |
| 5,641,906 A | * | 6/1997 | Moore ......................... 73/614 |
| 6,089,095 A | | 7/2000 | Yang et al. |
| 6,424,597 B1 | * | 7/2002 | Bolomey et al. ............ 367/138 |
| 6,938,488 B2 | * | 9/2005 | Diaz et al. .................... 73/597 |
| 7,107,852 B2 | * | 9/2006 | Hutchins et al. .............. 73/598 |
| 7,683,479 B2 | * | 3/2010 | Yazawa ...................... 257/727 |

FOREIGN PATENT DOCUMENTS

JP         58011384       *   1/1983

* cited by examiner

*Primary Examiner*—Jacques M Saint Surin
(74) *Attorney, Agent, or Firm*—Frank R. Niranjan

(57) ABSTRACT

An ultrasonic test apparatus includes a container containing de-ionized water, a pressing member, a supporting member, and a fixing member. The limiting member, the loading member, and the cover member are disposed in the de-ionized water. The fixing member tightly fixes the pressing member and the supporting member together for mounting at least part of integrated circuits to be detected between the pressing member and the supporting member.

13 Claims, 4 Drawing Sheets

ULTRASONIC TEST APPARATUS

BACKGROUND

1. Field of the Invention

The present invention generally relates to ultrasonic test apparatuses, and particularly to an ultrasonic test apparatus for inspecting integrated circuits.

2. Description of Related Art

Integrated circuits (IC) are widely used in electronic devices. The ICs are fabricated and then packaged. However, during pre-packaging the ICs are tested for defects including crack and de-lamination etc., caused by environmental conditions. In order to detect these defects, ultrasonic test apparatuses are used.

Generally, an ultrasonic test apparatus includes a transmitting transducer and a receiving transducer. An IC to be tested for defects is separated from but between the transmitting transducer and the receiving transducer. During test, the transmitting transducer emits ultrasonic waves to the IC. The ultrasonic waves pass through the IC and are received by the receiving transducer on the other side of the IC. Certain defects (such as cracks or de-lamination) can cause certain changes (amplitude and/or phase) in the electrical signals. As such, if the electrical signals are measured when the IC is subjected to ultrasonic waves, certain defects of the IC can be identified. However, if the IC is not stably held during the ultrasonic test, noise may be induced due to vibrations or jitters. Such noise would affect the detection precision of the defects. That is, the ultrasonic test apparatus may not accurately measure the degree of defects of the IC.

Therefore, in order to accurately detect the defects, the IC should be stable and free from vibrations or jitters. Thus, providing an ultrasonic test apparatus satisfying this requirement is desired.

SUMMARY

An ultrasonic test apparatus for detecting defects in integrated circuits is provided. The ultrasonic test apparatus operates by projecting ultrasonic waves from a transmitting transducer and receiving exiting ultrasonic waves passing through or reflected from the integrated circuits by a receiving transducer. The ultrasonic test apparatus includes a container containing de-ionized water, a supporting member, at least one pressing member, and a fixing member disposed in the de-ionized water, and located between the transmitting transducer and the receiving transducer. The supporting member is configured for at least partially pressing the integrated circuits to be detected. The fixing member is configured for tightly fixing the pressing member and the supporting member together for mounting at least part of the integrated circuits between the pressing member and the supporting member.

Other advantages and novel features will become more apparent from the following detailed description of exemplary embodiment when taken in conjunction with the accompanying drawings.

DETAILED DESCRIPTION

Figure 1:
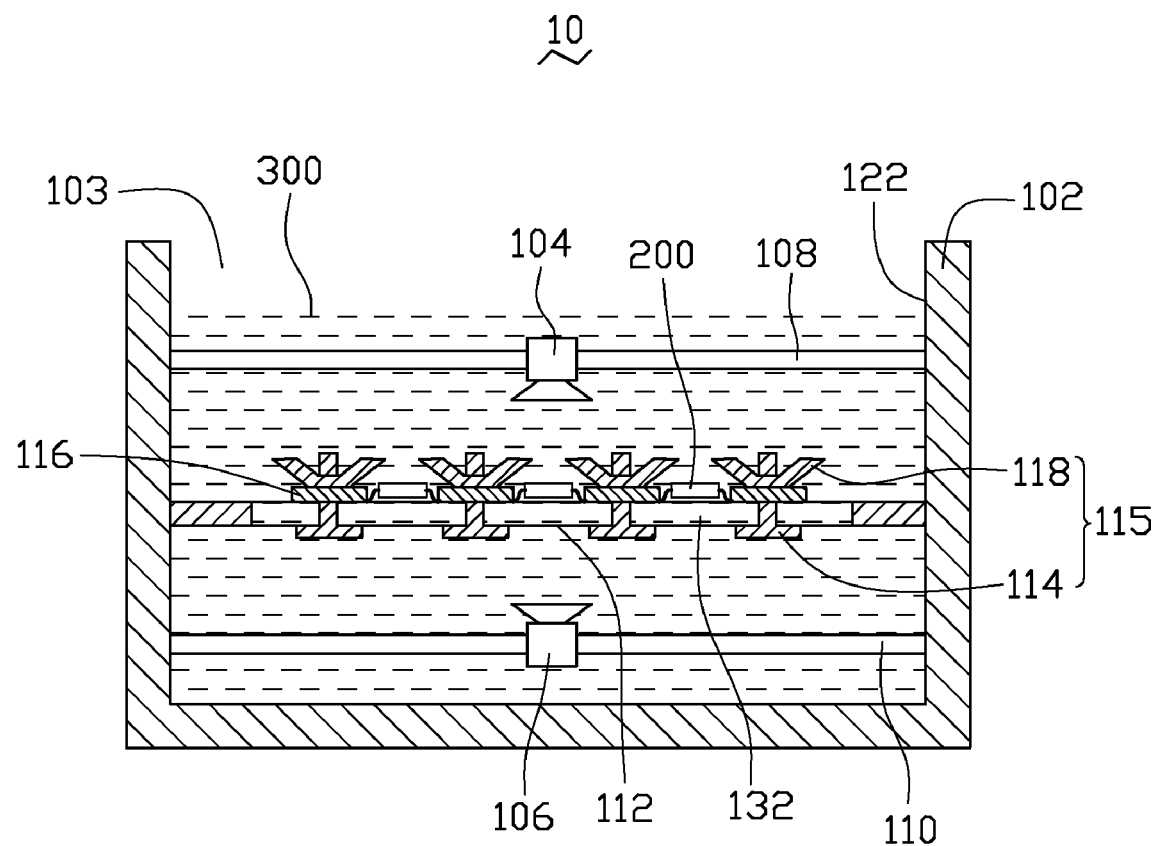
FIG. 1 is a sectional view of a first ultrasonic test system in accordance with an exemplary embodiment.
Figure 2:
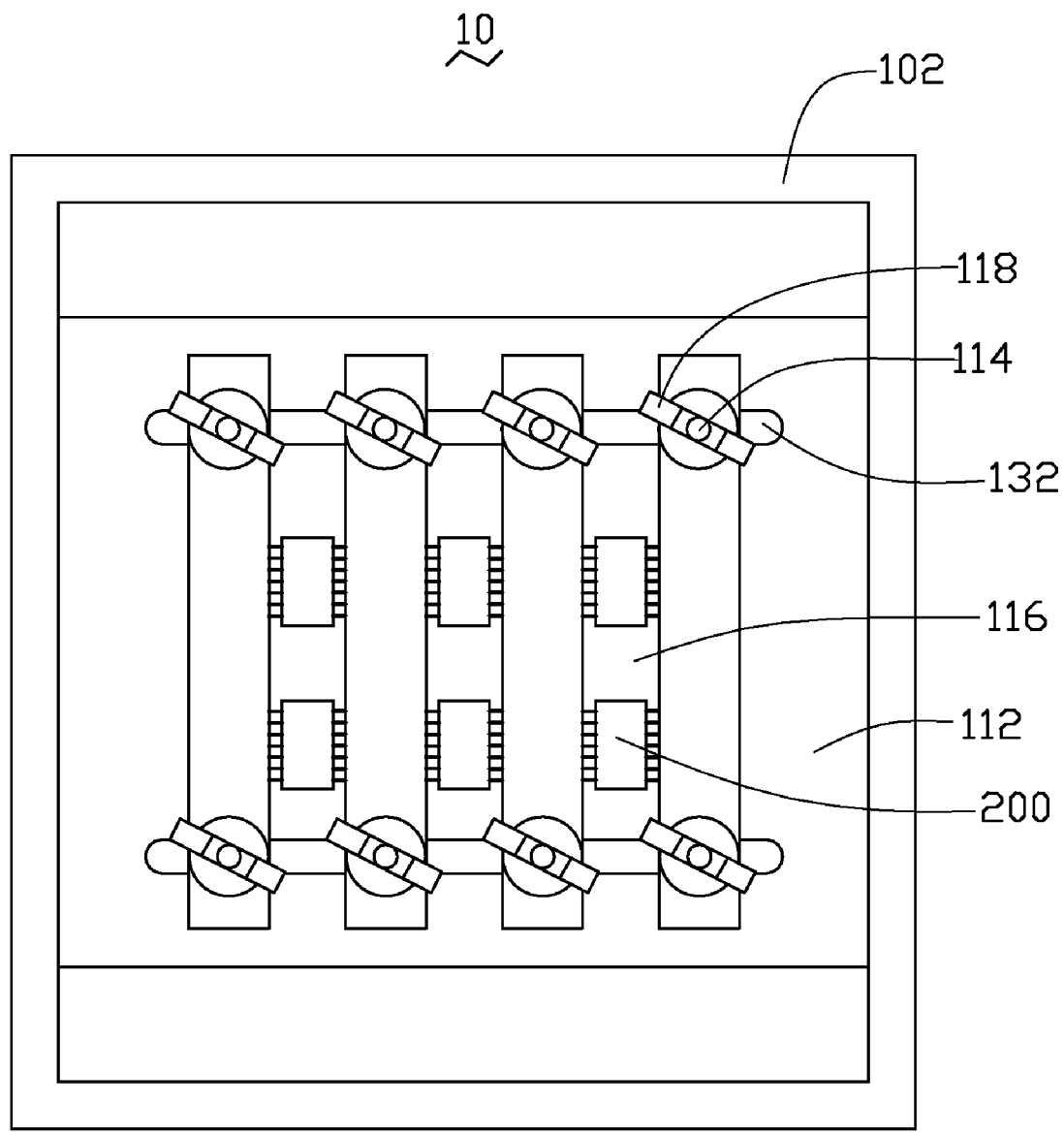
FIG. 2 is a partially top view of the ultrasonic test system shown in FIG. 1.
Figure 3:
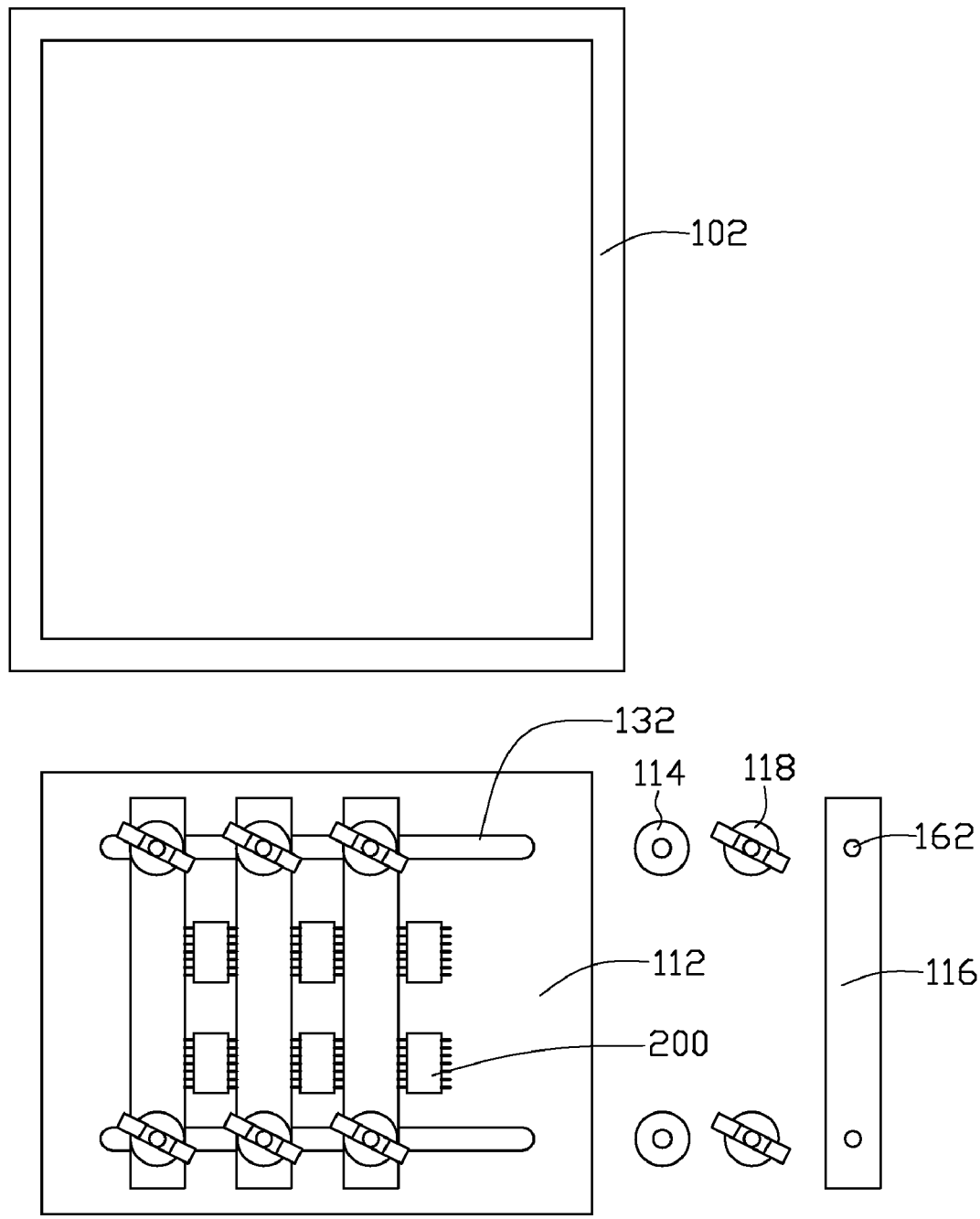
FIG. 3 is an partially exploded top view of the ultrasonic test system shown in FIG. 1.

Referring to FIGS. 1-3, a first ultrasonic test apparatus 10 in accordance with an exemplary embodiment is illustrated. The first ultrasonic test apparatus 10 is provided for detecting defects of cracks and de-lamination in integrated circuits (IC) 200. The first ultrasonic test apparatus 10 includes a container 102, a transmitting transducer 104, a receiving transducer 106, a first positioning member 108, a second positioning member 110, a supporting member 112, a plurality of pressing members 116, and a plurality of fixing members 115.

The container 102 defines a cavity 103 for accommodating de-ionized water 300. The de-ionized water 300 acts as a transmission medium for ultrasonic waves.

The transmitting transducer 104 is configured for projecting ultrasonic waves at predetermined frequencies. The receiving transducer 106 is configured for receiving ultrasonic waves that passed through the ICs 200. The receiving transducer 106 is also configured for providing electrical signals, converted from the received ultrasonic waves, to computers (not shown) for detecting the defects. The transmitting transducer 104 and the receiving transducer 106 are attached to the first positioning member 108 and the second positioning member 110 respectively.

The first positioning member 108, and the second positioning member 110 are disposed parallel to each other, and are connected to internal side walls of the container 102. The first positioning member 108 is configured for moving the transmitting transducer 104 along a first plane indicated by O-XY coordinate plane (see FIG. 2) over the ICs 200, such that a plurality of ICs 200 can be scanned. The second positioning member 110 is configured for moving the receiving transducer 106 in synchronization with the transmitting transducer 104 along a second plane parallel to the first plane O-XY, for receiving corresponding ultrasonic waves from the transmitting transducer 104.

The supporting member 112 is mounted between two internal side walls on opposite sides of the container 102, and are located between the first positioning member 108 and the second positioning member 110. The supporting member 112 is substantially a rectangular plate for placing the ICs 200 to be detected thereon. The supporting member 112 defines a pair of elongated slots 132 adjacent to two sides of the supporting member 112 other than the two sides mounted to the internal side walls of the container 102. The pair of elongated slots 132 are configured for receiving the plurality of fixing members 115.

Each of the fixing members 115 includes a screw 114 and a nut 118 that can be fastened together. The screw 114, fastened together with the nut 118, can be configured to slide along an extending direction of the elongated slot 132 to adjust a position corresponding to the IC 200 to be mounted. The pressing member 116 is strip-shaped, and is made of rubber material with elastic property. The pressing member 116 is configured for pressing a portion of the ICs 200. The pressing member 116 defines a pair of through holes 162 at opposite ends. The through holes 162 are configured for corresponding screws 114 of the fixing members 115 to pass through. As a result, the pressing member 116 can be locked with the supporting member 112 by tightly fastening the nut 118 with the screw 114.

During test, a plurality of ICs 200 are regularly placed on the supporting member 112. Each IC 200 is pressed by disposing two pressing members 116 on a portion such as conductive pins of the IC 200. Each screw 114 sequentially passes through the elongated slot 132 and the through hole 162 of the pressing member 116. The nut 118 is fastened to the screw 114 using utility tools. The pressing members 116 are tightly fixed to the supporting member 112 by the corresponding nuts 118 and screws 114, such that the ICs 200 are stably mounted.

After the ICs 200 are firmly mounted between the pressing member 116 and the supporting member 112 by the fixing member 115, the transmitting transducer 104 projects ultrasonic waves to the ICs 200. The ultrasonic waves travel through the ICs 200 from one side to another side. The receiving transducer 106 receives exiting ultrasonic waves from the ICs 200.

The receiving transducer 106 transforms the received ultrasonic waves to electrical signals, and sends the electrical signals to a computer (not illustrated) to detect the defects according to amplitude or phase information of the electrical signals. Because certain defects are known to cause certain changes or attenuation of amplitude and/or phase in the electrical signals, thus, certain defects in the ICs 200 can be detected according to the amplitude and/or phase information of the electrical signals.

The transmitting transducer 104 and the receiving transducer 106 are controlled by the positioning members 108, 110 to move in synchronization parallel to the O-XY coordinate plane, such that all portion of the ICs 200 can be scanned for detecting defects.

Figure 4:
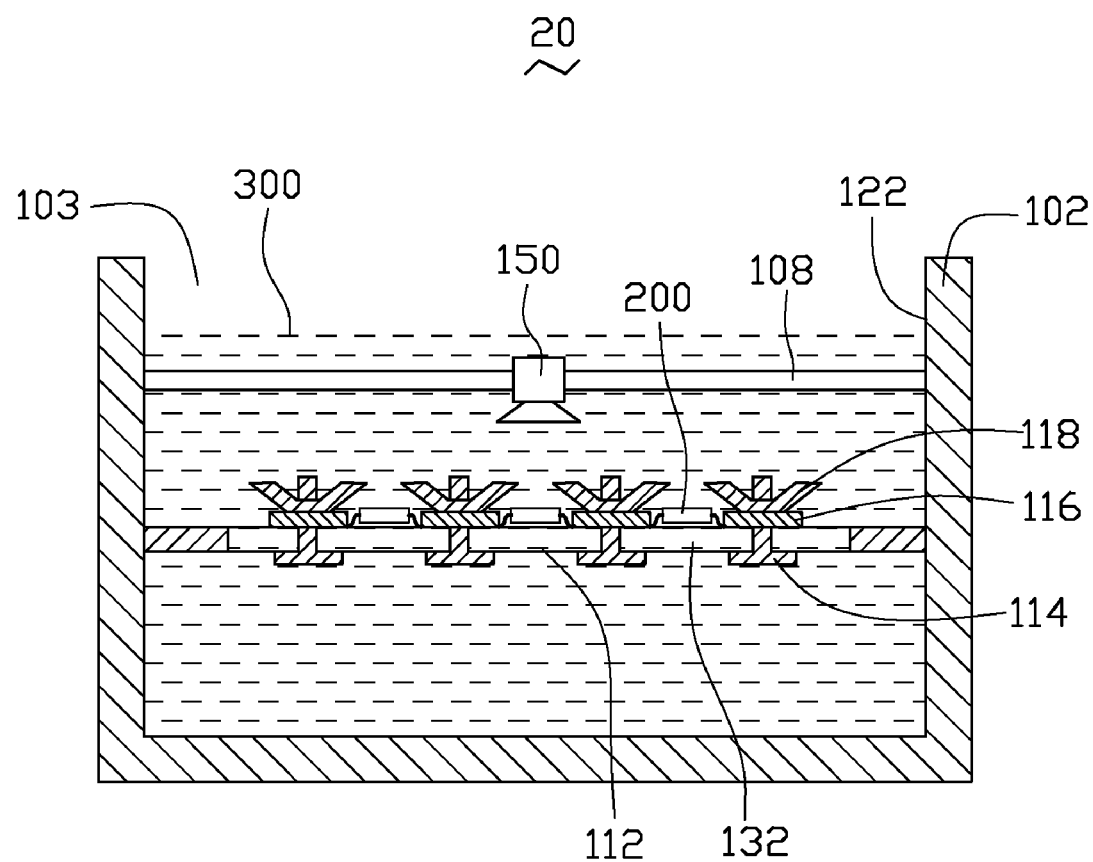
FIG. 4 is a sectional view of a second ultrasonic test system in accordance with another exemplary embodiment.

Referring to FIG. 4, a second ultrasonic test apparatus 20 in accordance with an alternative embodiment is illustrated. The second ultrasonic test apparatus 20 has similar configurations with the first ultrasonic test apparatus 10. A main difference between the first ultrasonic test apparatus 10 and the second ultrasonic test apparatus 20 is that the second ultrasonic test apparatus 20 includes a combination member 150 corresponding to the transmitting transducer 104 and the receiving transducer 106.

Furthermore, the second ultrasonic test apparatus 20 only includes one positioning member 108 for attaching the combination member 150 thereto. The combination member 150 not only projects ultrasonic waves to the IC 200 to be detected, but also receives echoed ultrasonic waves reflected from the IC 200. The combination member 150 also sends electrical signals transformed from received ultrasonic waves to the computer to detect the defects.

As described above, the first ultrasonic test apparatus 10 and the second ultrasonic test apparatus 20 utilize at least a fixing member 115 for firmly mounting at least one ICs 200 to be detected between the pressing member 116 and the supporting member 112. As such, mounting mechanism of the integrated circuits is improved. Moreover, noise due to vibrations or jitters are reduced or eliminated, and the detection precision of the defects is improved accordingly.

The foregoing description of the exemplary embodiments of the invention has been presented only for the purposes of illustration and description and is not intended to be exhaustive or to limit the invention to the precise forms disclosed. Many modifications and variations are possible in light of the above teaching. The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. An ultrasonic test apparatus for inspecting defects in integrated circuits by projecting ultrasonic waves from a transmitting transducer and receiving ultrasonic waves passing through or reflected from the integrated circuits by a receiving transducer to detect the defects, the ultrasonic test apparatus comprising:

a container for containing de-ionized water therein;

a first positioning member accommodated in the container, the first positioning member attaching the transmitting transducer thereto and for allowing the transmitting transducer slide therealong;

a second positioning member accommodated in the container and parallel to the first positioning member, the second positioning member attaching the receiving transducer thereto and for moving the receiving transducer therealong in synchronization with the transmitting transducer for scanning the integrated circuits;

a supporting member disposed in the de-ionized water, and located between the transmitting transducer and the receiving transducer, for supporting the integrated circuits to be detected thereon, the supporting member further defining at least one elongated slot, the at least one elongated slot extending in a direction parallel to the first and second positioning members;

at least one pressing member disposed in the de-ionized water, and located between the transmitting transducer and the receiving transducer, for at least partially pressing the integrated circuits to be detected; and a fixing member disposed in the de-ionized water, and located between the transmitting transducer and the receiving transducer, the fixing member extending through the at least one elongated slot and the at least pressing member to tightly fix the at least one pressing member and the supporting member together for mounting at least part of the integrated circuits between the at least one pressing member and the supporting member;

wherein the fixing member slides along the at least one elongated slot to drive the at least one pressing member and the integrated circuits to slide relative to the supporting member in a direction parallel to the first and second positioning members, and a position corresponding to the integrated circuit to be detected is adjusted.

2. The ultrasonic test apparatus of claim 1, wherein the fixing member comprises a screw and a nut, the screw and the nut are fastened for fixing the pressing member and the supporting member together.

3. The ultrasonic test apparatus of claim 2, wherein the pressing member defines at least one through hole for accommodating the screw.

4. The ultrasonic test apparatus of claim 1, wherein the pressing member is made of rubber material and has elastic property.

5. An ultrasonic test apparatus for detecting defects in integrated circuits, the ultrasonic test apparatus comprising:

a container defining a cavity for accommodating de-ionized water;

a first positioning member connected to two internal side walls of the container;

a combination member associated with the first positioning member, and driven by the first positioning member to move in at least two directions, the combination member projecting ultrasonic waves to the integrated circuits and receiving ultrasonic waves reflected from the integrated circuits;

a supporting member defining at least one elongated slot, the at least one elongated slot extending in a direction parallel to the first positioning member;

at least one pressing member; and at least one fixing member;

wherein the supporting member, the at least one pressing member, and the at least one fixing member are disposed in the de-ionized water, the integrated circuits to be tested is disposed on the supporting member, the fixing member extending through the at least one elongated slot and the at least one pressing member to tightly fix the pressing member and the supporting member together for mounting at least part of the integrated circuits between the pressing member and the supporting member.

6. The ultrasonic test apparatus of claim 5, wherein each fixing member comprises a screw and a nut, the screw and the nut are fastened for mounting the integrated circuits between the at least one pressing member and the supporting member.

7. The ultrasonic test apparatus of claim 6, wherein each pressing member defines at least one through hole for the screw passing through.

8. The ultrasonic test apparatus of claim 7, wherein the at least one pressing member is formed of rubber material and has elastic property.

9. The ultrasonic test apparatus of claim 5, further comprising:

two second positioning members for attaching the transmitting transducer and the receiving transducer thereto respectively, the two second positioning members being synchronized to move with the transmitting transducer for scanning the integrated circuits.

10. An ultrasonic test apparatus for detecting defects in an integrated circuit by projecting ultrasonic waves from a transducer assembly movably received in the ultrasonic test apparatus. the ultrasonic test apparatus comprising:

a support member for placing the integrated circuit to be detected thereon, the support member defining a pair of elongated slots, the elongated slots extending a direction substantially parallel to the movement direction of the transducer assembly;

a pair of pressing members disposed on conductive pins extending from two sides of the integrated circuit, each of the pressing member defining two through holes corresponding to each of the elongated slots; and a pair of fixing members slidably received in the elongated slots, the pair of fixing members extending through the elongated slots and the pressing members to fix the pressing member and the support member together for mounting the integrated circuit between the pressing member and the supporting member.

11. The ultrasonic test apparatus of claim 10, each fixing member comprises a screw and a nut, the screw passes through the elongated slot and the through hole sequentially for the nut fastening with the screw, such that the integrated circuits are mounted between the pressing member and the supporting member.

12. The ultrasonic test apparatus of claim 10, wherein the transducer assembly comprising a transmitting transducer for projecting ultrasonic waves and a receiving transducer for receiving the ultrasonic waves from the transmitting transducer.

13. The ultrasonic test apparatus of claim 12, further comprising:

a first positioning member attaching the transmitting transducer thereto and for allowing the transmitting transducer slide therealong; and a second positioning member attaching the receiving transducer thereto and allowing the receiving transducer slide therealong, the receiving transducer moved by the second positioning member in synchronization with the transmitting transducer for scanning the integrated circuits.

* * * * *